United States Patent
Kecht et al.

(10) Patent No.: US 9,581,540 B2
(45) Date of Patent: Feb. 28, 2017

(54) SPECTRAL LUMINESCENCE STANDARD FOR THE NEAR INFRARED REGION

(71) Applicant: GIESECKE & DEVRIENT GMBH, Munich (DE)

(72) Inventors: Johann Kecht, Munich (DE); Kai Uwe Stock, Grunwald (DE)

(73) Assignee: GIESECKE & DEVRIENT GMBH, Munich (DE)

( * ) Notice: Subject to any disclaimer, the term of this patent is extended or adjusted under 35 U.S.C. 154(b) by 87 days.

(21) Appl. No.: 14/357,301

(22) PCT Filed: Nov. 7, 2012

(86) PCT No.: PCT/EP2012/004625
§ 371 (c)(1),
(2) Date: May 9, 2014

(87) PCT Pub. No.: WO2013/068102
PCT Pub. Date: May 16, 2013

(65) Prior Publication Data
US 2014/0284497 A1  Sep. 25, 2014

(30) Foreign Application Priority Data
Nov. 9, 2011 (DE) .................. 10 2011 118 057

(51) Int. Cl.
*G01N 21/01* (2006.01)
*C03C 4/12* (2006.01)
(Continued)

(52) U.S. Cl.
CPC .............. *G01N 21/01* (2013.01); *C03C 4/12* (2013.01); *C03C 8/02* (2013.01); *C03C 8/08* (2013.01);
(Continued)

(58) Field of Classification Search
CPC .......... G01N 21/64; G01N 21/01; C03C 4/12; C03C 8/02; C09K 11/745; C09K 11/7774; C09K 11/7777
See application file for complete search history.

(56) References Cited

U.S. PATENT DOCUMENTS 4,598,205 A   7/1986  Kaule et al.
7,608,551 B2* 10/2009  Margaryan ............... C03B 5/08
                                                           501/44
(Continued)

FOREIGN PATENT DOCUMENTS

DE   29 10 827 A1   9/1979
DE   199 17 887 A1  1/2001
(Continued)

OTHER PUBLICATIONS

Jinjun Ren et al., "Effect of various alkaline-earth metal oxides on the broadband infrared luminescence from bismuth-doped silicate glasses", Solid State Communications, vol. 140, pp. 38-41, Jul. 19, 2006. www.elsevier.com/locate/ssc.
(Continued)

*Primary Examiner* — David Porta
*Assistant Examiner* — Mindy Vu
(74) *Attorney, Agent, or Firm* — Workman Nydegger

(57) ABSTRACT

A spectral luminescence standard has bismuth in a light-transmissive inorganic matrix material and emits light in the near infrared region upon irradiation with excitation light. The bismuth acts as a luminescence emitter in the near infrared region. A method includes manufacturing such a spectral luminescence standard and a calibration medium which has the spectral luminescence standard in or on a carrier material.

18 Claims, 3 Drawing Sheets

(51) Int. Cl.
    *C09K 11/74*    (2006.01)
    *C09K 11/77*    (2006.01)
    *C03C 8/02*     (2006.01)
    *C03C 8/08*     (2006.01)
    *D21H 21/30*    (2006.01)
    *D21H 21/48*    (2006.01)
    *G01N 21/64*    (2006.01)

(52) U.S. Cl.
    CPC ........ *C09K 11/745* (2013.01); *C09K 11/7774* (2013.01); *C09K 11/7777* (2013.01); *D21H 21/30* (2013.01); *D21H 21/48* (2013.01); *G01N 21/64* (2013.01)

(56) References Cited

U.S. PATENT DOCUMENTS

| | | |
|---|---|---|
| 7,999,237 B2 | 8/2011 | Schwenk et al. |
| 8,695,397 B2 | 4/2014 | Sacquard et al. |
| 2001/0000622 A1 | 5/2001 | Reeh et al. |
| 2009/0111207 A1 | 4/2009 | Choumane et al. |
| 2010/0163747 A1 | 7/2010 | Schwenk et al. |
| 2010/0171076 A1 | 7/2010 | Furusawa et al. |
| 2010/0304059 A1 | 12/2010 | Besson et al. |
| 2011/0174051 A1 | 7/2011 | Sacquard et al. |

FOREIGN PATENT DOCUMENTS

| | | |
|---|---|---|
| DE | 102008048043 A1 | 3/2010 |
| WO | 2006005498 A1 | 1/2006 |

OTHER PUBLICATIONS

Chinese Search Report from CN Application No. 201280054984.0, May 29, 2015.
International Search Report from corresponding International PCT Application No. PCT/EP2012/004625, Nov. 30, 2012.
International Preliminary Report on Patentability from corresponding International PCT Application No. PCT/EP2012/004625, May 13, 2014.
German Search Report Corresponding to German Application No. 10 2011 118 057.9, Feb. 25, 2013.

* cited by examiner

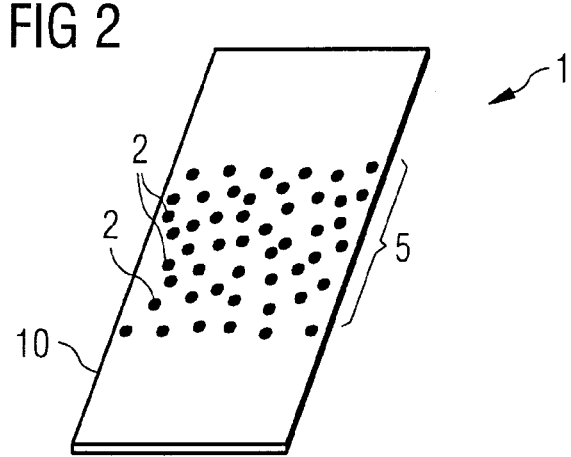
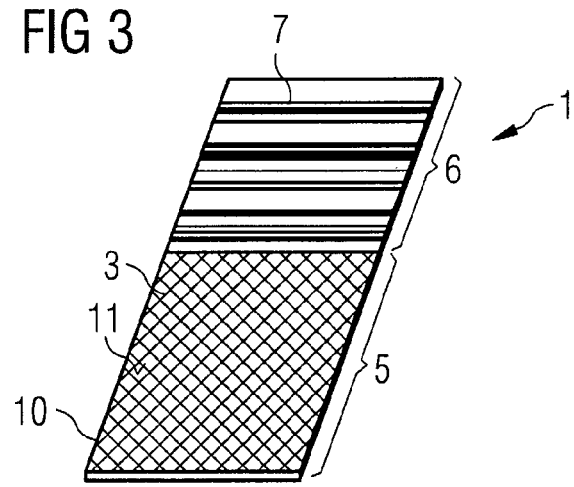
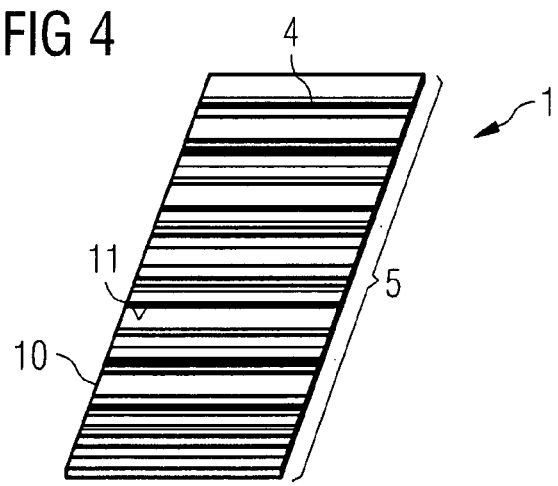

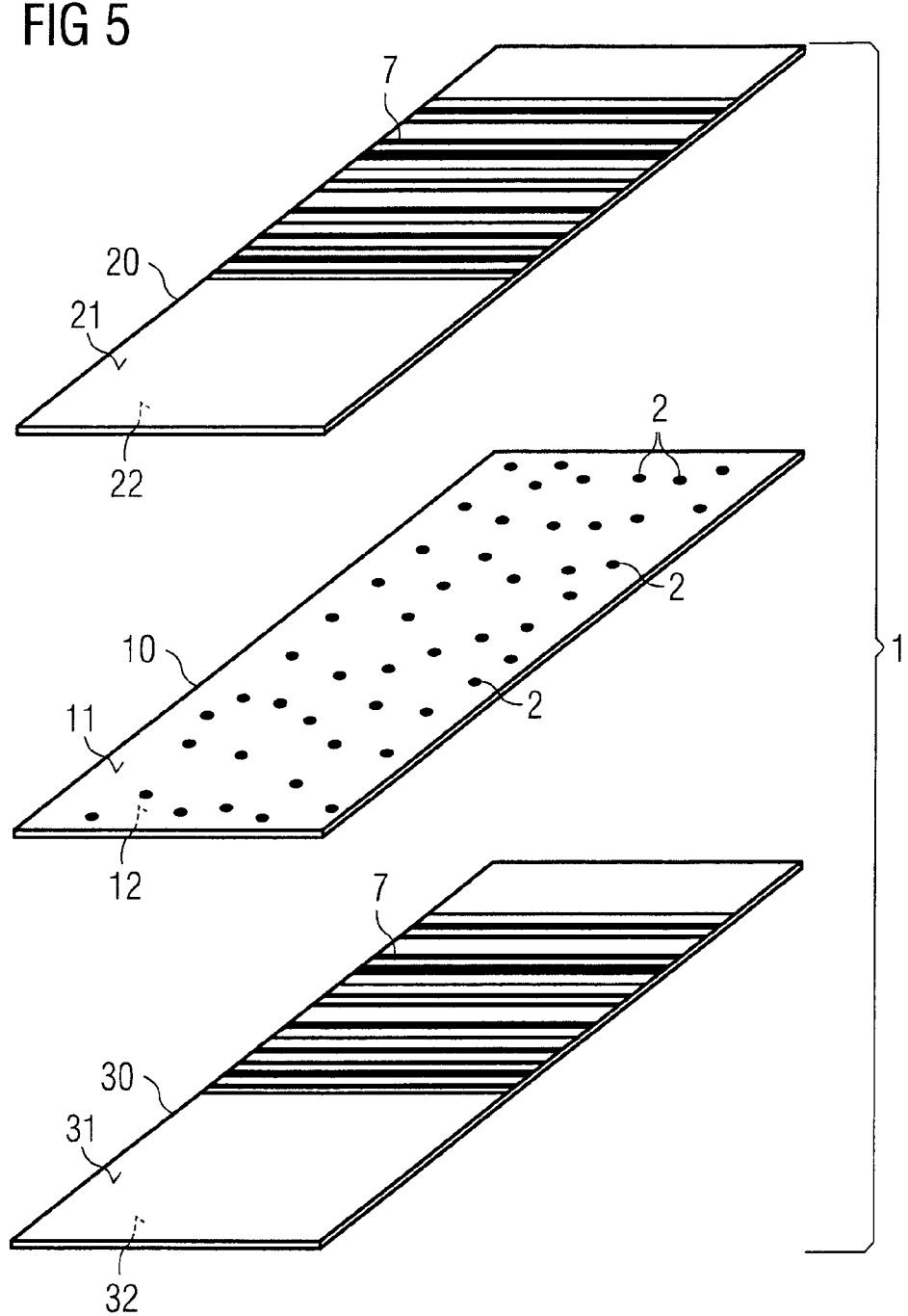

SPECTRAL LUMINESCENCE STANDARD FOR THE NEAR INFRARED REGION

BACKGROUND

The invention relates to a spectral luminescence standard with broadband emission in the near infrared region, to a method for manufacturing the luminescence standard, and to calibration media for calibrating optical testing devices or sensors, which exhibit the spectral luminescence standard or have it associated therewith.

SUMMARY

Value documents, such as bank notes, checks, ID documents, credit cards, deeds, and the like are frequently equipped with luminescent security features for securing authenticity. These security features are normally tested several times over the course of the lifespan of a value document.

Already upon manufacturing of the value documents or of the security papers which are employed for manufacturing the value documents, the correct incorporation or application of the luminescent substances must be tested. This is typically effected by installing a luminescence testing device at a suitable point of the production line of a security-paper material-web. The material web is transported through the various production sections with the aid of a transport system, and in so doing also transported past the stationary installed luminescence testing device which detects measurement signals of the material web during the transport.

Value documents in circulation, in particular bank notes, are tested in sheet material processing machines for their authenticity and/or their state, among other things also for their luminescent authenticity features.

For this purpose, the value documents are guided past a corresponding luminescence testing device which detects the luminescence signals emitted by the value document.

Here, however, the problem arises that the detected luminescence signals are subjected to device-dependent influences, which even may change in the course of time, so that a comparison of luminescence measurements, which were obtained with different devices, is not possible. Hence, defined reference systems are needed, which deliver certain target-value specifications, so-called luminescence standards. The luminescence testing devices can be calibrated or adjusted with the aid of the luminescence standards, so that the measurements of different devices, and at different times, are comparable with each other.

For calibrating a luminescence testing device which is arranged along the transport path of a material web, for example a material web for security papers or value documents, and is used for testing the material web upon the manufacturing thereof, usually a calibration medium is placed in the measuring plane of the testing device, in order to detect with the testing device a calibration measurement value of the calibration medium. For this purpose, the calibration medium can be manually presented—during an interruption of the material web test—to the testing device, so that, temporarily, instead of the material web, the calibration medium is placed in the measuring plane of the testing device. The calibration medium is a luminescence standard or contains a luminescence standard. The calibration medium has associated therewith a certain target value, which the testing device ideally detects upon a measurement of the calibration medium. In the real case, there is often ascertained a deviation of the actual measurement value from this target value. Then, the testing device must be re-adjusted, so that the measurement value of the testing device corresponds to the target value belonging to the calibration medium. As an alternative to manually presenting the calibration medium to the testing device, the calibration medium can also be transported past the testing device, so that a plurality of calibration measurement values of the calibration medium can be detected and for the calibration of the testing device an average value of these measurement values can be used. This allows a more exact calibration.

In sheet material processing machines such as apparatuses for value document processing, wherein for example bank notes are tested for authenticity, the value documents in the apparatus are usually transported past sensors, for example luminescence sensors. To calibrate the sensors, a suitable calibration medium, instead of the value documents, is transported past the sensors, the sensors sensing measurement values of the calibration medium. The calibration medium is a luminescence standard or contains a luminescence standard. The measurement values are compared with target values which are associated with the calibration medium. If the measurement values deviate from the target values, the sensor must be adjusted, until it delivers, upon a new measurement of the calibration medium, at least approximately the target values. Then the sensor can again be employed for testing value documents.

The requirements for a luminescence standard vary depending on the intended use. If a luminescence standard is to be employed as a calibration medium for calibrating sensors used for testing sheet material, it should be possible for the luminescence standard to be provided in the form of a sheet-shaped calibration medium. Also with respect to the optical properties there are different requirements. For example, basically, one has to distinguish between absorption standards which represent reference systems for measurements of the absorption behavior of luminescent substances, and luminescence standards which represent reference systems for measurements of the emission behavior of luminescent substances. Wavelength standards (reference systems for testing the wavelength accuracy) must have as many narrow bands as possible, while spectral standards must have as wide, smooth and unstructured spectra as possible. For all the standards applies that they should have a high homogeneity and isotropy and a low temperature dependence, should be long-term stable and photostable and should work with as high a quantum yield as possible.

The prior art offers broadband-emitting spectral luminescence standards for the visible region, but hardly any substances with broadband and unstructured emission in the near infrared region. The near infrared region (NIR region) is the wavelength region between 760 nm and 2500 nm.

For securing the authenticity of value documents, there are employed, among other things, substances which emit in the region between 1000 nm and 1500 nm. For this region, however, there have hitherto not been available any spectral luminescence standards, i.e. luminescence standards which emit broadband and unstructured luminescence upon irradiation with excitation light of a suitable wavelength, in particular any spectral luminescence standards which are suitable for employment as luminescence standards for calibrating luminescence sensors or luminescence testing devices in sheet material processing machines or paper machines.

Hence, it is the object of the present invention to provide a spectral luminescence standard for the region of 1000 nm to 1500 nm, i.e. a luminescence standard which at least in the region of 1000 nm to 1500 nm has wide, unstructured luminescence emissions.

It is also the object of the invention to state a method for manufacturing such a luminescence standard.

Furthermore, it is the object of the invention to provide a calibration medium which has a spectral luminescence standard for the region of 1000 nm to 1500 nm and is suitable for calibrating testing devices or sensors, e.g. luminescence sensors in sheet material processing machines or luminescence testing devices in paper machines.

The object is achieved by the spectral luminescence standard having the features as stated in claim 1, by the method for manufacturing the luminescence standard having the features as stated in claim 7, and by the calibration medium having the features as stated in claim 10. Embodiments of the invention are stated in the respective dependent claims.

The luminescence standard according to the invention has bismuth as a luminescence emitter. The luminescence properties of bismuth (III), which emits in the visible region, have been known for a long time. The present invention, however, does not employ bismuth (III) as an NIR luminescence emitter, but rather a Bi-species with broadband emission in the near infrared region (NIR region), the existence of said species being basically known although its exact identity is not completely clarified. In the technical literature there are discussed $Bi^+$, $Bi^{2+}$, $Bi^{5+}$, smaller cationic or neutral Bi-clusters (e.g. $Bi_2^{2+}$), BiO-radicals, as well as anionic bismuth species (e.g. $Bi_2^-$, $Bi_2^{2-}$). There are in particular indications of the presence of reduced cationic or neutral Bi-species. For use of the properties of this Bi-species within the framework of the present invention, the clarification of their identity, however, is not necessary. It is only essential that the bismuth species can be reliably and reproducibly manufactured. Suitable conditions for manufacturing this NIR-active Bi-species (NIR-Bi) are known. The formation of NIR-active Bi requires in particular high temperatures and stabilization in a matrix.

Upon irradiation with excitation light, the luminescence standard emits light in the near infrared region, the NIR-active bismuth acting as a luminescence emitter. The light emission of the luminescence standard in the near infrared region does therefore not stem from a trivalent Bi(III), but from the above-mentioned NIR-active Bi-species. The spectral width (FWHM) of the light emission in the near infrared region of the NIR-active species is at least 100 nm, preferably at least 200 nm. The excitation light may be e.g. in the visible spectral region or in the near infrared region, which, energetically, lies above the near infrared emission of the NIR-active Bi-species.

Suitable matrix materials are for example glasses, in particular silicate glasses, aluminum silicate glasses, borosilicate glasses, phosphate glasses, germanate glasses, and besides such oxide glasses also sulphide glasses. In principle, as matrix formers, i.e. starting materials for forming the matrix of NIR-active Bi, there are suitable all inorganic substances and substance mixtures, of which at temperatures above about 900° C. materials can be obtained by melting or sintering, in which NIR-active Bi can be stabilized and which are sufficiently light-transmissive, in particular optically transparent, for the excitation radiation and the luminescence emission radiation of NIR-active Bi. Optical homogeneity and transparency is relatively simplest to be achieved with glasses and glass-like materials, but this is not a mandatory requirement of the present invention. Also crystalline and semi-crystalline matrices are suitable, as long as it is ensured that they stabilize the bismuth species NIR-Bi broadband-emitting in the near infrared region and have sufficient transparency for excitation and emission of the fluorescence radiation.

Suitable starting materials (matrix formers) for manufacturing the matrix material are for example oxides, such as they are usually employed upon the manufacture of glass. Depending on the glass type, main constituents of the glasses are silicon oxide ($SiO_2$), boron oxide ($B_2O_3$), phosphorus oxide ($P_2O_5$), and germanium oxide ($GeO_2$). These main constituents normally are present in combination with several minor constituents in different quantitative shares. A "main constituent" is understood herein to be the constituent, which, in mole % of its oxide, has the relatively greatest share in the total composition. Various components can serve in some glasses as a main constituent, but in others as a minor constituent. For example boron oxide in combination with silicon oxide forms borosilicate glasses, and aluminum oxide in combination with silicon oxide forms aluminum silicate glasses.

In the present invention silicate glasses or aluminum silicate glasses contain about 50 to 90 mole % $SiO_2$ and 0 to 40 mole % $Al_2O_3$. Borate glasses and phosphate glasses contain about 30 to 90 mole % $B_2O_3$ or 30 to 90 mole % $P_2O_5$. Moreover, as minor constituents there can be contained alkaline metal oxides and/or alkaline-earth metal oxides and/or rare-earth metal oxides.

Alkaline metals, in particular lithium, increase the luminescence intensity of NIR-active Bi. $Li_2O$ is contained in the matrix materials of the present invention preferably in quantitative shares of up to 15 mole %, while $Na_2O$ and $K_2O$ in certain matrix material compositions may weaken the luminescence intensity and are employed preferably in quantitative shares of respectively less than 5 mole %.

Alkaline metals generally improve the properties of glasses, but MgO, CaO, SrO and BaO may in some cases weaken the luminescence properties, i.e. the emissivity, of NIR-active Bi and are therefore used in quantitative shares of the matrix material of likewise preferably less than 5 mole % (Mg, Ca, Sr, Ba)O.

In the present invention, preferred minor constituents of the matrix materials are rare-earth metals, in particular neodymium (Nd), dysprosium (Dy), holmium (Ho), erbium (Er), thulium (Tm) and ytterbium (Yb). The rare-earth metals can be employed singly or in combination. In the matrices they are present as trivalent cations and act as sensitizers, i.e. they absorb excitation energy and transfer it to the NIR-active Bi, whose excitation is made easier thereby. A spectral shift of the luminescence band of NIR-active Bi does not occur thereby. However, the emission spectrum can nevertheless be extended by doping the matrices with suitable rare-earth metals, namely by superposition of rare-earth metal emission-bands with the emission spectrum of NIR-active Bi. In accordance with a preferred embodiment of the present invention, the matrices are doped both with neodymium and with ytterbium, thereby the short-wave end of the emission band even further extending into the short-wave region by superposition with the Nd- and Yb emission bands. Moreover, through this doping an excitation of the Bi-emission over the Nd- and Yb-absorption bands is enabled. In particular, by doping with Nd and Yb there can be achieved an extension of the luminescence emission in the short-wave near infrared region up to wavelengths of about 850 nm. Vice versa, in accordance with a further preferred embodiment of the present invention, by doping with thulium and holmium, the long-wave end of the emission band is extended even further into the long-wave region by superposition with the Tm- and Ho-emission bands. Therefore, a doping with Tm and Ho can be employed to achieve an extension of the luminescence emission in the long-wave near infrared region up to wavelengths of more than 2 μm.

Rare-earth metal oxides should be contained in shares of a maximum of 15 mole % (rare-earth metal oxides in total) of the matrix material. In case of higher shares, concentration quenching may impair the luminescence. Moreover, the addition of certain rare-earth metals, such as for example Ce, should be avoided. Potentially redox-active substances such as Ce may prevent the formation of NIR-active Bi.

Further preferred minor constituents which improve the luminescence intensity of NIR-active Bi are $TiO_2$ and $ZrO_2$, which can be contained preferably in quantitative shares of respectively up to 5 mole % of the matrix material. In quantitative shares of respectively preferably less than 1 mole % of the matrix material there can be contained $As_2O_3$, $Sb_2O_3$, $SnO_2$ and $Fe_2O_3$. These metals prevent a reduction or oxidation of NIR-active Bi and promote its formation. The same applies to $Al_2O_3$, which in particular in silicate glasses promotes the formation of NIR-active Bi. Aluminum oxide can be contained in significantly higher quantities, preferably in quantitative shares of about 10 to 30 mole % of the matrix material.

Bismuth is employed in the present invention in a quantitative share, related to $Bi_2O_3$, of 0.01 to 10 mole %, preferably 0.5 to 5 mole % of the luminescence standard (bismuth plus matrix material).

The starting materials for manufacturing the luminescence standard according to the invention are in principle not limited in any way, but preferably oxides and carbonates or mixtures thereof are employed. This is due to the easy availability and/or processability of these substances.

A particularly preferred spectral luminescence standard according to the present invention has NIR-active Bi in a glass matrix, the luminescence standard containing 1 to 3 mole % $Bi_2O_3$, 75 to 90 mole % $SiO_2$, 10 to 20 mole % $Al_2O_3$, 0.1 to 0.5 mole % $Nd_2O_3$ and 1 to 5 mole % $Yb_2O_3$.

The stated chemical formulas regarding the constituents of the luminescence standard relate to the starting materials for manufacturing the luminescence standard. In particular the constituent $Bi_2O_3$ is employed as a starting material for manufacturing the luminescence standard. Through the manufacturing process of the luminescence standard, from the $Bi_2O_3$ at least partly the NIR-active Bi-species is formed. In the finished luminescence standard, the Bi stemming from the $Bi_2O_3$ is at least partly converted into the NIR-active Bi-species emitting in the near infrared.

Hereinabove, oxidic matrix materials such as oxide glasses have been described. However, it is expressly pointed out that the matrix materials by no means need to be of oxidic nature. Rather, also other inorganic matrices are suitable for stabilizing NIR-active Bi, in particular sulphide glass.

Further, not only glasses come into consideration as matrix materials, but also semi-crystalline matrices and crystalline matrices such as for example glass ceramics and minerals. Preferred mineral matrices for the present invention are zinc spinel ($ZnFe_2O_4$), cesium iodide (CsI) and barium diphosphate ($Ba_2P_2O_7$).

Preferably, also crystalline, porous matrix materials (ion exchangers), such as zeolites and layer silicates, can be loaded with $Bi^{3+}$-cations, and then be activated at elevated temperatures through formation of the NIR-Bi-species. In so doing, the crystalline structure usually is destroyed, however, and there arise similar products as with a glass melt.

For manufacturing a spectral luminescence standard according to the invention, the starting materials, for example oxides (where applicable in combination with carbonates) for glass manufacturing or minerals in powder-form are well mixed, where applicable compacted with addition of some water, again well mixed and dried. If amorphizable inorganic ion exchanger materials such as zeolites and/or layer silicates are employed as starting materials for the matrix, bismuth is not added in the form of an oxide, carbonate etc. in powder-form, but first there is carried out an ion exchange with a suitable bismuth salt, i.e. the matrix precursor is filled with bismuth cations in the desired quantity. The filled ion exchanger is then washed, dried, where applicable further comminuted, and like the starting materials, which are desired in powder-form, compacted and dried. The drying is effected preferably at a temperature of about 40 to 80° C. for about 10 to 15 hours. Then, the homogeneous mixture is annealed in a suitable crucible, for example, in a corundum crucible or a platinum crucible. For the formation of NIR-active Bi, relatively high annealing temperatures of the starting materials are necessary. When using a corundum crucible, it is to be taken into account that in some cases a reaction with the crucible material may take place, which influences the final composition or the aluminum content of the product. The necessary annealing temperatures depend on whether one works under inert gas (for example nitrogen or argon) or in air. Upon heating under inert gas atmosphere, already a temperature of about 900° C. can be sufficient for the production of NIR-active Bi, while upon heating in air, temperatures of about 1300° C. to 1800° C. are required. According to the invention, one works preferably in air.

The starting material mixture is slowly heated (heating rate about 2° C. to 4° C. per minute) to the desired end temperature, held at this temperature for at least about 3 hours, preferably for at least about 4 hours, and then slowly cooled down to room temperature. The cooling rate is preferably about 1° C. to 3° C. per minute.

Upon the annealing process one obtains, depending on starting materials and annealing conditions, a glass melt or a sintered body. Minerals such as for example zeolites often yield sintered bodies which are amorphized through the high temperatures. The cooled-down glass or the cooled-down sintered body is now comminuted to a suitable particle size, for employment in the calibration media according to the invention in flat material form, particle sizes of less than 50 μm being preferred. The comminution can be effected for example by dry grinding or wet grinding in a mill. The comminution has the additional advantage that spatially spectrally slightly inhomogeneous products are homogenized. A high spatial homogeneity is often hard to achieve in luminescence standards in the form of a continuous glass body. The luminescence standard is comminuted, according to the invention, preferably to a powder with a grain size of less than 20 μm. This small grain size guarantees a particularly good spectral homogeneity as well as incorporativity in calibration media according to the invention.

An annealing at elevated temperature is the preferred manufacturing method for the NIR-active bismuth species. It is also possible, however, to produce the NIR-active Bi-species by irradiating bismuth-containing matrices with gamma radiation or energy-rich electron radiation. This makes it possible for the NIR-active Bi-species to be formed at room temperature. Elevated temperatures are then unnecessary or may even have a disturbing effect through the reformation of the formed species.

In the prior art there are known luminescence standards in the form of glass panes with defined thickness, in the form of powders, in the form of powder additions to lacquer formulations and polymers, etc. The luminescence standard according to the invention can of course be used in these forms, but its particular advantage is, among other things, the fact that it is excellently suited for employment in or on sheet-shaped calibration media. Sheet-shaped calibration media are required, as mentioned above, to calibrate luminescence sensors and luminescence testing devices in paper machines and sheet material processing machines, in particular spectral calibration media for the NIR region being required. The luminescence standard according to the invention with NIR-active Bi in an inorganic matrix material is excellently suited for these purposes.

Calibration media according to the invention (luminescence standard plus carrier) have a carrier flat-material of paper or of plastic or of both. The carrier flat-materials have a thickness in the range of preferably about 50 to 300 μm, particularly preferably about 100 μm. The luminescence standard according to the invention is either incorporated in the volume of the carrier material or represents a coating on one or on both surfaces of the carrier material. When the luminescence standard is incorporated in the volume of the carrier material, the carrier material should be not or only weakly absorbent, i.e. it must be sufficiently transmissive at least for the luminescence emission of the NIR-active Bi and the excitation wavelengths to make possible a well detectable luminescence emission. The quantity of luminescence standard incorporated in the volume of the carrier material preferably lies in the range of about 1 to 20 wt. % of the carrier material, particularly preferably at about 5 wt. % of the carrier material. If the luminescence standard is applied in the form of a printing ink or ink composition or similar liquid composition onto a surface of the carrier material, in order to form a coating, for the dry coating comparable quantities of luminescence standard are valid, i.e. the share of the luminescence standard related to the carrier material then preferably amounts to about 1 to 10 wt. % (concentrated on the surface of the carrier material).

The calibration media according to the invention have e.g. the form of a sheet of a defined size, for example the size of a value document to be tested in a sheet-material processing machine. The sheet of defined size can also be provided for being attached to a sheet carrier, which may facilitate the handling of the calibration medium. In the case of a sheet of defined size, the luminescence standard may extend, integrated in the volume of the carrier material or as a coating on a surface, over the entire area of the sheet or only over a certain region thereof. The sheet may additionally contain specifications about the luminescence target-value of the luminescence standard, it being possible for these specifications to be made available through the spatial arrangement of the luminescence standard, for example in the form of a barcode. Of course, the target-value specifications for the luminescence can also be made available in a different form, for example as a separate barcode beside or on the areal region of the luminescence standard.

The calibration medium can have the luminescence standard also in a spatial arrangement, which allows correcting misorientations upon the positioning of the calibration medium, as it is specified in DE 10 2008 048 043 A1, to whose disclosure in this regard reference is hereby made. Further, a calibration medium according to the invention can be used for further calibrations and have corresponding further standards, such as for example wavelength standards, standards for other optical sensors or testing devices or standards for the calibration of sensors or testing devices for other security features such as magnetic security features or others.

BRIEF DESCRIPTION OF THE DRAWINGS

The invention will hereinafter be illustrated further on the basis of Figures. It is pointed out that the Figures are not true to proportion and not true to scale. Moreover, there are represented respectively only the features essential for understanding the present invention. It is obvious that there can be present additional features or that the represented features can also be employed in other combinations as represented in a specific Figure. The same reference numbers designate respectively the same or corresponding elements. There are shown.

DETAILED DESCRIPTION OF VARIOUS EMBODIMENTS

Figure 1:
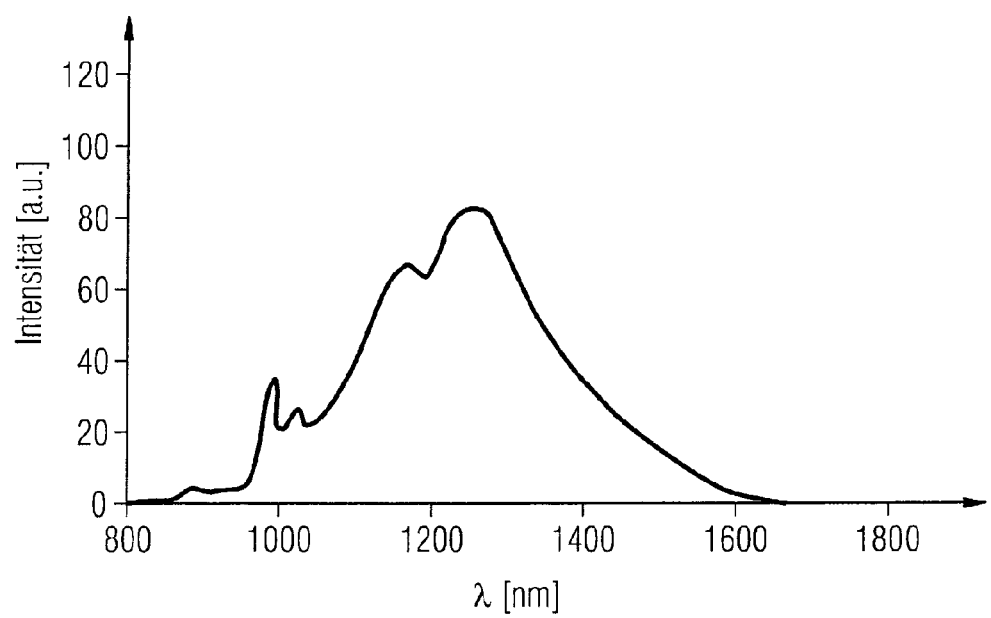
FIG. 1 an emission spectrum of a spectral luminescence standard according to the invention, and FIGS. 2 to 5 respectively schematic representations of different embodiments of a calibration medium according to the invention.

FIG. 1 shows the emission spectrum of the luminescence standard according to a first embodiment, which was obtained from a glass of the composition of $(Bi_2O_3)_{1.55}(Al_2O_3)_{14.2}(SiO_2)_{84.3}(Nd_2O_3)_{0.159}(Yb_2O_3)_{3.18}$. The luminescence standard is contained in a paper carrier-medium. The spectral luminescence standard of the invention has been manufactured as follows: 8.46 g $Bi_2O_3$, 0.626 g $Nd_2O_3$ and 14.67 g $Yb_2O_3$ have been pre-homogenized in the mortar. 59.30 g $SiO_2$ (Evonik GmbH, Sipernat 50S) and 16.95 g $Al_2O_3$ (Sigma-Aldrich, 4N nanopowder) have been added and all the components well mixed, then the powder compacted by addition of water, anew mixed, and the mixture dried at 60° C. for 12 h. The dried mixture has been heated in a corundum crucible with a ramp of 3° C./min to 1600° C., held 4 h at 1600° C., and then again brought to room temperature with a ramp of 2° C./min.

The red-violet glass obtained thereby has been coarsely comminuted, and then dry grinded in an agate mill for 120 minutes, in order to obtain a glass powder with a medium grain size D99=20 μm. For manufacturing a calibration medium according to the invention this powder has been added to a cellulose paper pulp in such a quantity that, upon the sheet manufacturing, in the final paper of the thickness of 100 μm a relative mass share of spectral luminescence standard of 5 wt. % has been achieved. The luminescence standard according to the invention is excited in particular over the absorption bands of Nd, e.g. with a wavelength of 595 nm, and the sheet-shaped calibration medium has the emission spectra represented in FIG. 1. The intensity of the emission is stated in arbitrary units (a. u.), and it is apparent that the emissions begin already at wavelengths below 900 nm and end only in the region above 1600 nm. Emission intensities usable for a calibration lie in the wavelength region between 900 and 1600 nm.

The intensity of the spectrum has been measured at 2400 different points of the sheet sample with a measuring spot of the size 1 $mm^2$. A low standard deviation of 7% from the mean value has been ascertained thereby. The sheet-shaped, flexible calibration medium thus has a high homogeneity.

According to a second embodiment, the luminescence standard is manufactured on the basis of a germanate glass. Suitable quantity ranges are in particular 1-2 $Bi_2O_3$; 3-20

$Al_2O_3$; 80-96 $GeO_2$ (all information in mole %). The luminescence standard is obtained e.g. from a glass of the composition $(Bi_2O_3)_{0.9}(Al_2O_3)_6(GeO_2)_{93.1}$. For the manufacturing thereof 3.89 g $Bi_2O_3$, 5.68 g $Al_2O_3$ and 90.4 g $GeO_2$ have been homogenized in the mortar. Then the powder has been compacted by addition of water, mixed anew, and the mixture dried at 60° C. for 12 h. The dried mixture has been heated in a corundum crucible with a ramp of 3° C./min to 1600° C., held 4 h at 1600° C., and then again brought to room temperature with a ramp of 2° C./min. The material obtained has been coarsely crushed, and dry grinded in an agate mill until a glass powder with a medium grain size D99 below 20 μm has been obtained. For manufacturing a calibration medium according to the invention this powder has been added to a cellulose paper pulp in such a quantity that, upon the sheet manufacturing, in the final paper of the thickness of 100 μm a relative mass share of spectral luminescence standard of 7 wt. % has been achieved. The luminescence standard according to the invention can be excited, among other things, over the absorption bands of the NIR-active Bi-species, for example at 500 nm. The broadband emission begins already at wavelengths of below 1000 nm and ends in the region above 1600 nm. Emission intensities usable for a calibration lie in the wavelength region between 1000 nm and 1600 nm.

According to a third embodiment, the luminescence standard is manufactured on the basis of a phosphate glass. Suitable quantity ranges are in particular 0.5-2 $Bi_2O_3$; 10-25 $Al_2O_3$; 70-90 $P_2O_5$; 1-3 $Yb_2O_3$ (all information in mole %). The luminescence standard is obtained e.g. from a glass of the composition $(Bi_2O_3)_{1.2}(Al_2O_3)_{20}(P_2O_5)_{76.8}(Yb_2O_3)_2$. For the manufacturing 2.65 g $Bi_2O_3$, 9.69 g $Al_2O_3$, 83.9 g $NH_4H_2PO_4$, 3.74 g $Y_2O_3$ and 2 g activated carbon (for setting the annealing atmosphere) have been homogenized in the mortar. The mixture has been heated in a corundum crucible with a ramp of 3° C./min to 1600° C., held 4 h at 1600° C., and then again brought to room temperature with a ramp of 2° C./min. The material obtained has been coarsely crushed, and dry grinded in an agate mill until a glass powder with a medium grain size D99 below 20 μm has been obtained. For manufacturing a calibration medium according to the invention this powder has been added to a cellulose paper pulp in such a quantity that, upon the sheet manufacturing, in the final paper of the thickness of 100 μm a relative mass share of spectral luminescence standard of 6 wt. % has been achieved. The luminescence standard according to the invention is excited, among other things, over the absorption bands of Yb, for example at 980 nm. The broadband emission begins already at wavelengths below 1000 nm and ends in the region above 1500 nm. Emission intensities usable for a calibration lie in the wavelength region between 1000 and 1500 nm.

FIG. 2 shows a schematic representation of an embodiment of a calibration medium 1 according to the invention. The calibration medium 1 has a sheet-shaped carrier material 10, for example made of a paper. The carrier material 10 of course can alternatively consist of a plastic material, and it can be single-ply or multi-ply. Integrated in the volume of the carrier material 10, there are located particles 2 of the spectral luminescence standard according to the invention. In the represented embodiment, the luminescence-standard particles 2 are located only in a partial region 5 of the carrier material 10, while in the other regions there is space for any further standards and/or target-value specifications. It is obvious, that the carrier material 10 must be sufficiently transmissive at least for wavelengths in the range of the excitation wavelengths and of the emission wavelengths of the luminescence standard, in order to ensure an appropriate excitation of the luminescence standard and an appropriate detectability of the emissions.

FIG. 3 shows an alternative embodiment of a calibration medium according to the invention. Here, the carrier material 10 has in a partial region 5 of its first surface 11 a coating 3 made of a luminescence standard according to the invention. For manufacturing the coating 3, the spectral luminescence standard according to the invention is suspended for example in finely powdered form in a carrier medium and printed onto the carrier material 10. In the region 6 of the first surface 11 of the carrier material 10 there is printed with a conventional printing ink a barcode 7. The barcode 7 indicates the luminescence target-value of the luminescence standard to be detected in the region 5. The coating 3 and the barcode 7 can also be provided on both surfaces of the carrier material 10.

FIG. 4 shows a further alternative embodiment of a calibration medium 1 according to the invention. In this embodiment, the carrier material 10 has on its entire first surface 11 a barcode 4, which consists of a print of the spectral luminescence standard according to the invention. For this purpose, the luminescence standard is again prepared and printed as an ink or printing ink. The barcode 4 in this case simultaneously delivers the emission spectrum for calibrating a testing device as well as the specification of the target value to be detected. It is obvious, that the print 4 can also be provided on both surfaces of the carrier material 10, in order to allow a simultaneous calibration of sensors or testing devices that are arranged opposite each other. Such an opposite arrangement is often to be found in sheet material processing machines, so that both surfaces of a bank note or of another value document can be tested simultaneously. Of course, the barcode 4 does not have to extend, as represented in FIG. 4, respectively over a complete surface of the carrier material 10, but can also cover only partial regions of a surface.

FIG. 5 shows a further alternative embodiment of a calibration medium 1 according to the invention. In this embodiment, the calibration medium 1 consists of a sheet-shaped carrier material 10, in the volume of which luminescence-standard particles 2 are incorporated. In the embodiment represented here, in the entire volume of the carrier material 10 there are located luminescence-standard particles 2. The carrier material 10 is sufficiently transmissive at least for wavelengths in the range of the excitation wavelengths and of the emission wavelengths of the luminescence standard, in order to ensure an appropriate excitation of the luminescence standard and an appropriate detectability of the emissions. For example, a carrier material 10 made of paper or plastic can be employed, which is light-scattering, but also sufficiently light-transmissive.

The calibration medium 1 has two further carrier materials 20, 30, e.g. plastic foils, with the same dimensions as the carrier material 10. The carrier material 20 has a first surface 21 and a second surface 22, and is connected on the second surface 22 with the first surface 11 of the carrier material 10, for example adhesively bonded. The carrier material 30 has a first surface 31 and a second surface 32, and is connected on the first surface 31 with the second surface 12 of the carrier material 10, for example adhesively bonded. On the first surface 21 of the carrier material 20, as well as on the second surface 32 of the carrier material 30 there are respectively located prints 7 in the form of barcodes which specify the target value of the luminescence standard of the invention to be detected by a luminescence testing device. The carrier materials 20, 30 are otherwise light-transmissive, e.g. transparent, for excitation radiation and emission radiation of the luminescence standard, respectively. The target-value barcode-print 7 is, at least for the emission radiation of the luminescence standard, however, not light-transmissive, but light-absorbent. Of course, also possibly employed adhesives are not or only weakly absorbent.

If now the calibration medium 1 is guided past one or past two mutually opposing luminescence sensors or luminescence testing devices, the sensors or testing devices detect, upon scanning the calibration medium 1, a plurality of calibration measurement values. In the case of the calibration medium of FIG. 5, these measurement values, however, can only be detected in the barcode interstices, since the barcode stripes even absorb the light emitted by the luminescence standard, provided that they have admitted an excitation of the luminescence standards at all. The barcode thus ensures a modulation of the measurement values detected by the sensors or by the testing devices. This modulation is decoded by the sensors or testing devices, in order to ascertain one or several target values which are associated with the calibration medium 1 and required for the calibration. In the case of the calibration medium of FIG. 4, the calibration measurement values are detected, vice versa, only on the stripes of the barcode 4.

The represented embodiments of the calibration medium according to the invention as a flexible sheet which has the spectral luminescence standard of the invention in its volume or as a print on a surface, represent the preferred embodiments of the present invention, as they are particularly suited for testing the functionality of spectrally broadband sensor means of paper testing machines for special paper. Sheet-shaped calibration media can be introduced themselves, like the papers to be tested, into the testing machines, for example via the transport rollers of the testing machines. In finely comminuted form distributed in or on a sheet-shaped carrier material, the spectral luminescence-standard materials of the invention also have a particularly high homogeneity. Further advantages of the luminescence standards of the invention or calibration media having the luminescence standards of the invention are the high chemical stability, long-time storage stability and light resistance of the luminescence standards.

The invention claimed is:

1. A spectral luminescence standard for calibrating a luminescence testing device, comprising: bismuth in a light-transmissive, optically transparent, inorganic matrix material,
    wherein the luminescence standard emits light in the near infrared region upon irradiation with excitation light, and bismuth acts as a luminescence emitter in the near infrared region,
    wherein the luminescence standard has a broadband luminescence emission in the near infrared region; and
    wherein the luminescence standard is a powder with a grain size of less than 50 μm.

2. The spectral luminescence standard according to claim 1, wherein the inorganic matrix material is a silicate glass, an alumosilicate glass, a borosilicate glass, a borate glass, a phosphate glass, a germanate glass or a sulphide glass.

3. The spectral luminescence standard according to claim 1, wherein the inorganic matrix material has at least one alkaline metal and/or at least one alkaline-earth metal for increasing the luminescence intensity.

4. The spectral luminescence standard according to claim 1, wherein the inorganic matrix material is doped with at least one rare-earth metal, except for Ce.

5. The spectral luminescence standard according to claim 1, wherein the inorganic matrix material has silicon, aluminum, bismuth, neodymium, ytterbium and, alkaline metals or alkaline-earth metals in the composition, related to the oxides, of 75 to 90 mole % $SiO_2$, 10 to 20 mole % $Al_2O_3$, 1 to 3 mole % $Bi_2O_3$, 0.1 to 0.5 mole % $Nd_2O_3$, 1 to 5 mole % $Yb_2O_3$.

6. A method for manufacturing a spectral luminescence standard according to claim 1 comprising the following steps:
    intimately mixing an inorganic bismuth compound with at least one matrix former for manufacturing a bismuth-containing mixture; or
    filling an amorphizable inorganic ion exchanger material with bismuth cations for manufacturing a bismuth-containing ion exchanger,
    heating the bismuth-containing mixture or the bismuth-containing ion exchanger under inert gas at 900° C. to 1800° C. or in air at 1300° C. to 1800° C. for at least 3 hours; and
    leaving to cool down an obtained melt or a sintered product and comminuting the cooled-down melt or the sintered product to a powder of a grain size below 50 μm.

7. The method according to claim 6, wherein the bismuth compound and the matrix formers are used as oxides and/or carbonates.

8. The method according to claim 6, wherein to the bismuth-containing mixture or to the bismuth-containing ion exchanger at least one alkaline metal and/or at least one alkaline-earth metal and/or at least one rare-earth metal is added in the form of an oxide, of a carbonate, of a sulphate, or of a nitrate.

9. A calibration medium having
    a spectral luminescence standard according to claim 1 and
    a carrier material for the luminescence standard.

10. The calibration medium according to claim 9, wherein the carrier material is sheet-shaped, and the spectral luminescence standard is contained in the volume of the carrier material or in a partial region of the volume of the carrier material.

11. The calibration medium according to claim 9, wherein the carrier material is sheet-shaped, and the spectral luminescence standard is provided as a coating over the full area or over a partial area on one or on the two surfaces of the carrier material.

12. The calibration medium according to claim 9, wherein the calibration medium has specifications regarding the spectral luminescence standard's luminescence target-value to be detected, the specifications being made available by the calibration medium having a barcode which effects a modulation of the luminescence signals detectable from the luminescence standard, the modulation corresponding to the luminescence target-value.

13. The calibration medium according to claim 12, wherein the specifications regarding the luminescence target-value to be detected at the barcode are made available through the spatial arrangement of the spectral luminescence standard on the carrier material.

14. The calibration medium according to claim 12, wherein it has at least on one surface of the carrier material a further sheet-shaped carrier material, which has light-transmissive regions and light-non-transmissive regions for excitation radiation and emission radiation of the luminescence standard, wherein the specifications regarding the luminescence target-value to be detected the barcode are made available through the spatial arrangement of the light-transmissive and the light-non-transmissive regions of the further sheet-shaped carrier material.

15. The spectral luminescence standard according to claim 1, wherein the luminescence standard is a powder with a grain size of less than 20 μm.

16. The spectral luminescence standard according to claim 1, wherein the luminescence standard has the broadband luminescence emission in the near infrared region of 1000 nm to 1500 nm.

17. The spectral luminescence standard according to claim 1, wherein a spectral width of the broadband luminescence emission in the near infrared region is at least 100 nm.

18. A calibration medium for calibrating a luminescence testing device, comprising:
- a spectral luminescence standard including bismuth in a light-transmissive, optically transparent, inorganic matrix material, wherein the luminescence standard emits light in the near infrared region upon irradiation with excitation light, and bismuth acts as a luminescence emitter in the near infrared region, and
- a carrier for the spectral luminescence standard, wherein the carrier material is sheet-shaped;
- wherein the calibration medium has specifications regarding the spectral luminescence standard's luminescence target-value to be detected, the specifications being made available by the calibration medium having a barcode which effects a modulation of the luminescence signals detectable from the luminescence standard, the modulation corresponding to the luminescence target-value.

* * * * *